United States Patent [19]
Bendel et al.

[11] Patent Number: 5,219,358
[45] Date of Patent: Jun. 15, 1993

[54] SHAPE MEMORY EFFECT SURGICAL NEEDLES

[75] Inventors: Lee P. Bendel, Lebanon; William C. McJames, Belle Mead; Walter McGregor, Flemington; Robert J. Tannhauser, Piscataway, all of N.J.

[73] Assignee: Ethicon, Inc., Somerville, N.J.

[21] Appl. No.: 751,903

[22] Filed: Aug. 29, 1991

[51] Int. Cl.5 .............................................. A61B 17/00
[52] U.S. Cl. ..................................... 606/222; 606/78; 606/139
[58] Field of Search ................... 606/222, 78, 223-227, 606/164, 76, 144, 148, 27, 28, 139; 148/402

[56] References Cited

U.S. PATENT DOCUMENTS

| | | | |
|---|---|---|---|
| 4,170,990 | 10/1979 | Baumgart et al. | 128/92 B |
| 4,425,908 | 1/1984 | Simon | 128/1 R |
| 4,485,816 | 12/1984 | Krumme | 128/334 |
| 4,926,860 | 5/1990 | Stice et al. | 606/144 |
| 4,984,581 | 1/1991 | Stice | 128/772 |
| 5,002,563 | 3/1991 | Pyka et al. | 606/222 |
| 5,037,433 | 8/1991 | Wilk et al. | 606/139 |
| 5,067,957 | 11/1991 | Jervis | 606/108 |
| 5,069,226 | 12/1991 | Yamauchi et al. | 128/772 |

OTHER PUBLICATIONS

Flexmedics Corporation; Nitinol . . . The Material of Choice for Safer, More Effective Medical Procedures; (Product Literature).

Concept Europe B.V.; LTS TM Long Term Suture; (Product Literature).

By Dieter Stoeckel and Weikang Yu; Superelastic Ni-Ti Wire; Wire Journal International, Mar. 1991.

*Primary Examiner*—Stephen C. Pellegrino
*Assistant Examiner*—Gary Jackson
*Attorney, Agent, or Firm*—Emil Richard Skula

[57] ABSTRACT

Surgical needles are fabricated from a shape memory alloy. The alloy has a low temperature state, in which the needle is formable into an elongated shape to pass through an elongated tube, and a high temperature state, in which the needle forms an arc. The needle is particularly adapted for use in endoscopic surgery. A needle that has a remembered curved shape is straightened and passed to a surgical site through a cannula. It is then returned to its curved shape by heating it at the surgical site. After use, it is withdrawn through the cannula.

5 Claims, 3 Drawing Sheets

SHAPE MEMORY EFFECT SURGICAL NEEDLES

BACKGROUND OF THE INVENTION

1. Field of the Invention

This invention relates to surgical needles that are fabricated from alloys that display shape memory and to methods for using such surgical needles.

2. Description of the Related Art

Shape memory, as the name implies, refers to the characteristic of certain metals that if the metals are deformed, they can be returned to their original shape simply by heating. Metal alloys that display this "shape memory effect" have been known for decades. Although early applications for these materials were primarily military, more recently the alloys have been used for a variety of applications, including medical.

Although a number of alloys display the shape memory effect, NiTi alloys (called Nitinol alloys) have found the greatest utility. Alloys that are approximately 50 (atomic) percent Ni and 50 percent titanium have found particularly widespread use.

U.S. Pat. No. 4,170,990, issued Oct. 16, 1979 to Baumgart et al., discloses a method for implanting into living tissue a mechanical connecting element fabricated from a shape memory alloy and ultimately removing the elements. Before implantation, the element is given a shape memory at a high temperature, then cooled and deformed for insertion. After implantation, the element is heated above a particular temperature to cause it to assume the shape it had prior to the plastic deformation. When the element is to be removed, it is cooled and returned to the shape it had for insertion.

U.S. Pat. No. 4,425,908, issued Jan. 17, 1984 to Simon, discloses a Nitinol blood clot filter, which in its low temperature phase can be straightened and passed through a tube or catheter, while being kept cool. When it reaches its destination in the body (e.g., the vena cava), the element is transformed to its high temperature state and takes on a remembered filter shape.

U.S. Pat. No. 4,485,816, issued Dec. 4, 1984 to Krumme discloses a shape memory surgical staple. The staple is first given a desired closed shape at an elevated temperature. It is then cooled and deformed into an open position. The open staple is then positioned so that it extends between and is in contact with portions of tissue to be joined together. On heating the staple, it assumes its remembered (closed) shape, penetrating and joining the tissue.

U.S. Pat. No. 4,926,860, issued May 22, 1990, to Stice et al., discloses arthroscopic instrumentation that takes advantage of the "superelasticity" inherent in shape memory alloys. Superelasticity (or "pseudoelasticity") describes the property of shape memory alloys that they return to their original shape upon unloading after a substantial deformation. The instrumentation may include a cannula having a curved lumen and a flexible shape memory alloy probe. The curved cannula is inserted into the body with its distal end adjacent an operative site. The probe is given a straight shape in the austenitic condition or the cold worked martensitic condition. Forced through the cannula, the probe bends elastically, but when it emerges from the distal end, it resumes its straight shape. The instrumentation permits a straight probe to reach a remote operative location that might otherwise be inaccessible to the probe. The probe may comprise a pair of SME needles attached at their proximal ends to opposite ends of a suture. Similar technology is disclosed in U.S. Pat. No. 4,984,581, issued Jan. 15, 1991 to Stice.

U.S. Pat. No. 5,002,563, issued Mar. 26, 1991 to Pyka et al., discloses sutures utilizing shape memory alloys. The sutures are given a loop shape at an elevated temperature, then cooled and deformed (straightened) to facilitate insertion into tissue. After the suture is in place, it is heated or otherwise transformed to its high temperature (loop) shape. Although the suture is generally attached to a needle for insertion, it can alternatively be sharpened to obviate the need for a needle. That technique presupposes that the alloy can be sharpened and penetrate tissue in its low temperature state.

SUMMARY OF THE INVENTION

In accordance with the present invention, a needle comprises a shape memory alloy, which has a first, low temperature state and a second, high temperature state, the needle
 (a) in its low temperature state being formable into an elongated shape to permit passage through an elongated tube and
 (b) in its high temperature state
  (i) forming a predetermined arc and
  (ii) being suited for use as a surgical needle.

The needle is particularly adapted for endoscopic and other surgical procedures in which elements are passed to the surgical site through a cannula that has a narrow lumen, which would not pass an ordinary curved rigid needle of the type that is needed or desired at the site.

For use in those procedures, a method for introducing a curved needle to a surgical site in a patient comprises the steps of:
 (a) inserting a cannula into the patient to permit access form outside the patient to the surgical site,
 (b) providing a shape-metal-alloy needle that, having been formed into an arc shape and tempered at an elevated temperature, has been formed into an elongated shape while in a first, low-temperature state,
 (c) passing the elongated needle through the cannula, and
 (d) heating the needle to a temperature at which the alloy is converted to a second, high-temperature state, thereby causing the needle to return tot he arc shape.

For convenience in this specification and the appended claims, we refer to the curved needle as being int he shape of an arc, although clearly the needle could have any "remembered" shape desired.

DETAILED DESCRIPTION OF THE INVENTION

Figure 4:
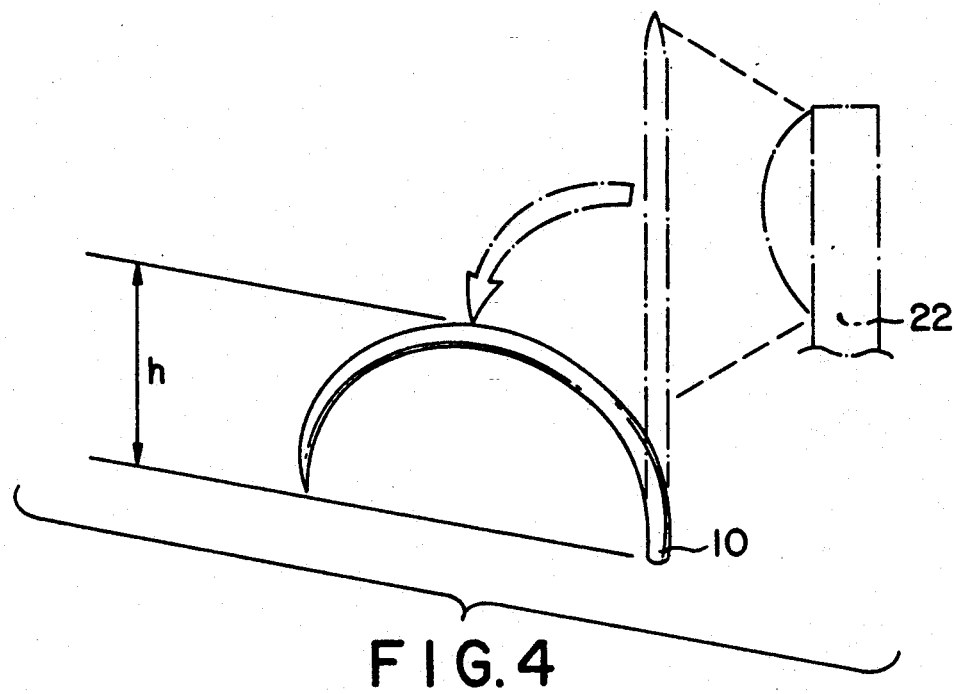
FIG. 4 is a schematic of a needle of the present invention being curved by a heater.

In recent years, a great deal of attention has been given to controlling the rapid rise of hospital and medical costs. In the surgical area, less-invasive procedures offer an opportunity not only to reduce costs but also to reduce patient trauma and speed recovery. A technique that has been developed in recent years to reduce the invasiveness of surgical procedures is endoscopic surgery.

Endoscopic surgery involves the use of an endoscope, an instrument that permits a surgeon to visually inspect any cavity of the body. The endoscope is inserted through a tube, conventionally referred to as a cannula, after a hole is punched into the soft tissue that protects the body cavity. The hole is made with a trocar, which is a sharp-pointed instrument. The trocar includes an obturator, or cutting implement, which slides within a trocar cannula. The obturator first punches a hole in the tissue about equal in size to the inner diameter of the cannula. The obturator is then withdrawn from the cannula. Often, two or more cannulas are inserted in this way, depending on the procedure that is to be done. Each cannula provides access to the surgical site for one or more functions; e.g., illumination, visualization, introduction of surgical devices, etc. The surgeon can then perform diagnostic and therapeutic procedures at the surgical site, using instrumentation designed to fit through the cannula(s).

From the standpoint of minimizing patient trauma, it is clearly desirable to minimize both the number and diameter of the cannula that are inserted into the patient. When the procedure involves surgery, it is generally necessary to join tissue at the surgical site. That requirement has led to a problem. Since the preferred surgical needles are in the shape of an arc, which is typically in the range of $\frac{1}{4}$ to $\frac{5}{8}$ of a circle (i.e. an arc whose interior angle is in the range of about 90°–225°), the preferred surgical needles cannot be passed through the preferred (i.e. narrow) cannulas to the surgical site.

It has now been determined that the shape memory effect (SME) provides the route to a solution to the problem. The basis of the SME is a phase change that takes place in certain alloys; i.e. shape memory alloys (SMAs), as they are cooled or heated through their characteristic transformation temperature. The best known SMAs are NiTi (Nitinol) alloys in which the phase change is from an ordered cubic crystal form above its transformation temperature (TTR) to a monoclinic crystal phase below the TTR. The transformation is known as a martensitic transformation between a high temperature "austenitic" form and a low temperature "martensitic" form. For a given alloy composition in a given annealed condition, the transformation takes place at a predictable, repeatable temperature. The transformation takes places when the alloy in one phase reaches a temperature at which the other phase is thermodynamically more stable. Because the change takes place by a shearing motion of the above, instead of by a diffusion mechanism, the transformation takes place virtually instantaneously.

Note that it is convenient to refer to a single TTR at which the phase transformation takes place. More precisely, an alloy becomes martensitic over a narrow temperature range as it is cooled through TTR and becomes austenitic over a narrow, and slightly higher temperature range as it is heated through TTR.

Figure 1:
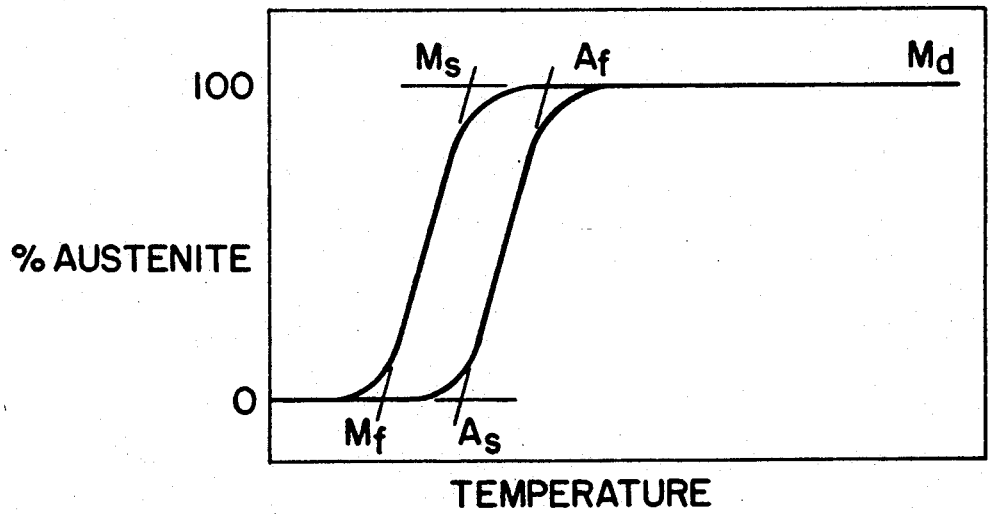
FIG. 1 depicts a hysteresis curve for a martensitic transformation in a shape memory alloy.

A curve (hysteresis curve) that depicts this behavior is shown as FIG. 1. On heating the alloy, the transformation to the high temperature austenitic phase begins at $A_s$ and is complete at $A_f$. On subsequent cooling, the alloy begins the martensitic transformation at $M_s$ and completes it at $M_f$. In order to induce in the alloy a shape that will be remembered, the alloy must be trained by constraining it in the desired shape and heating it to a temperature well above $A_f$.

Figure 1A:
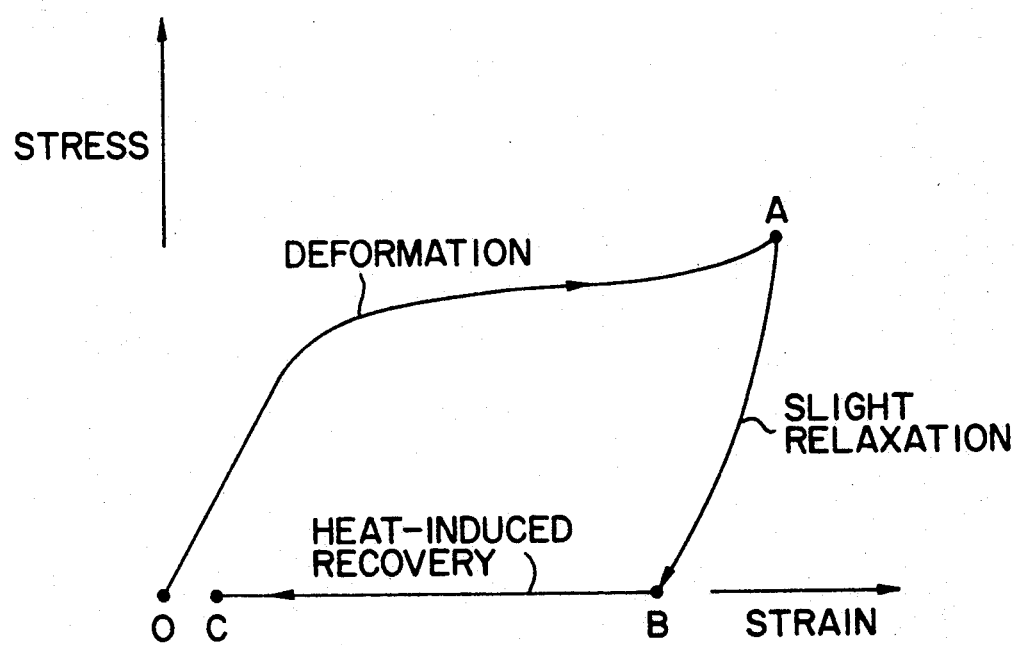
FIG. 1A depicts a stress-strain curve for the deformation and heat-induced recovery of a shape memory alloy.

Another way of viewing the behavior of SMAs uses the stress/strain curve of FIG. 1A. Beginning with the alloy in its remembered shape and martensitic phase at the origin "O", the alloy is deformed along the path O-A. When the deformation is complete (i.e. stress removed), the alloy relaxes slightly along the curve A-B. Heating the alloy to the austenitic phase returns it (nearly) to its original shape along the curve B-C.

The use of SMA's for surgical needles is as follows. A surgical needle is fabricated from a SMA into the desired "arc" shape. As used in this specification, and the appended claims, "arc" is meant to refer generally to a curved shape, although an arc of a circle is the shape most commonly used for a surgical needle. The arc is maintained at a temperature well above $A_f$ (FIG. 1) in the austenitic phase. The needle is then cooled below $M_f$, transforming to the martensitic phase. While in the martensitic phase, the needle is deformed (i.e., straightened) to the extent necessary to be able to pass through a cannula.

Figure 2:
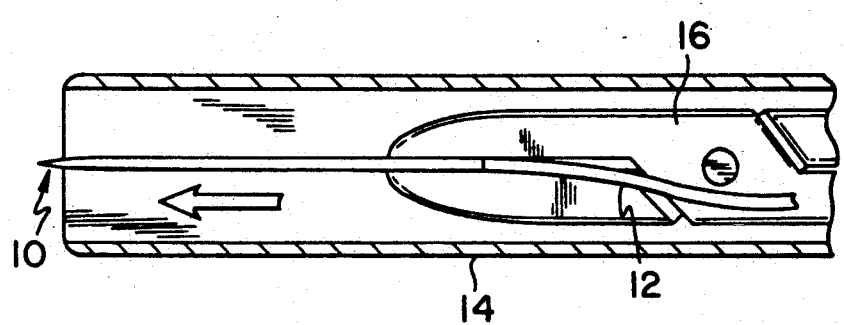
FIG. 2 depicts a needle of the present invention in a cross section of a cannula.

FIG. 2 depicts a deformed needle 10, with attached suture 12 being passed through cannula 14, while being held in needle holder 16. The needle is passed through the cannula while it is maintained at a temperature below $A_s$.

Figure 3:
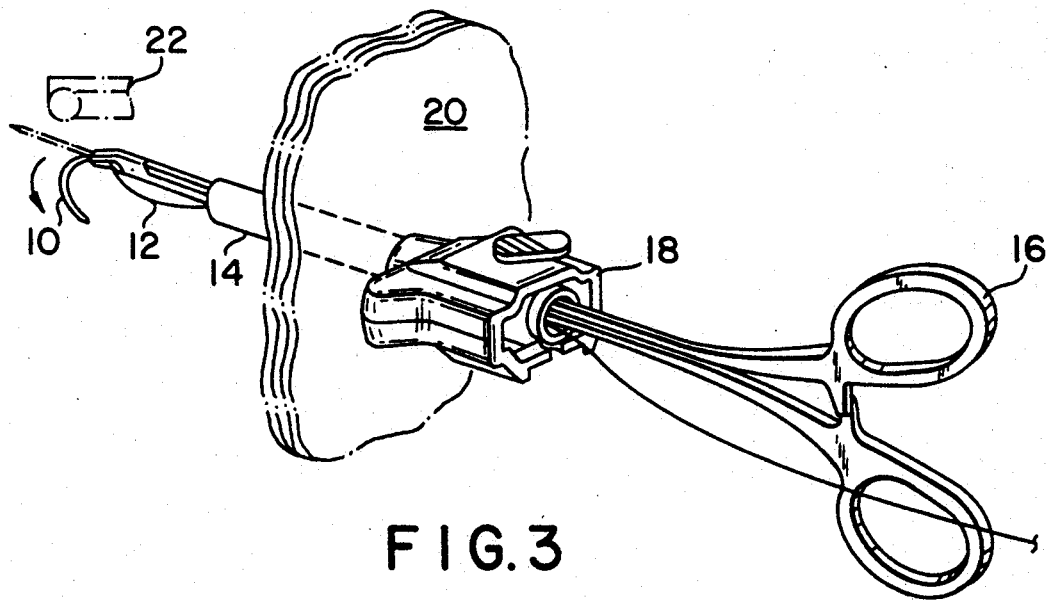
FIG. 3 is a perspective view of a needle of the present invention and the apparatus used to place it at a surgical site.

FIG. 3 shows a trocar 18, with attached cannula 14 in place, the obturator having been withdrawn. Needle 10, held in needle holder 16, is at the surgical site within the body. The body wall (skin) is shown schematically in cutaway section 20. Once at the surgical site, the needle is heated above $A_f$ with heater 22. Heat can be provided, for example, by an illumination light, by a laser, or by a cautery of any type used in endoscopic surgery. The needle is transformed to the austenitic phase and reverts to the curved shape. An enlarged schematic of the change in shape of needle 10, caused by heating with heater 22, is shown in FIG. 4.

Figure 5:
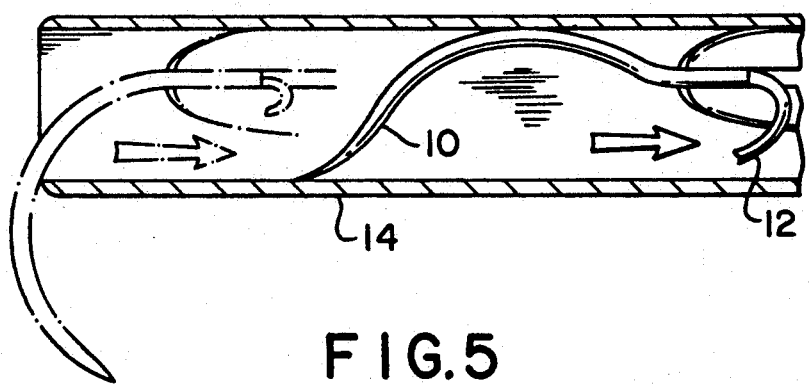
FIG. 5 depicts a needle of the present invention being withdrawn through a cross section of a cannula.

After the needle has performed its function at the surgical site, it is withdrawn through the cannula, as shown in FIG. 5. In the phantom view, needle 10 is shown as it is about to enter cannula 14. As needle 10 is pulled out through cannula 14, it deforms as shown in the solid line. Suture 12 is shown as having been cut to a very short length, for clarity and simplicity, although typically a longer length of suture remains attached to needle 10.

The inside diameter of cannulas used in endoscopy (and depicted in FIGS. 2, 3 and 5) is typically 5, 7 or 10 mm. The largest lateral dimension of a curved needle to be used at the surgical site, "h" in FIG. 4, may be as large as 12 mm. (Straightforward geometry shows that $h = R - \frac{1}{2}(4R^2 - L^2)^{\frac{1}{2}}$, where R is the radius of curvature and L the longitudinal dimension (i.e., the chord) of the curved needle.) If a surgeon tried to push such a needle through a 10 mm cannula, the needle point and/or cannula would be severely damaged. Possibly even worse, the needle could get stuck in the cannula, which would require that the cannula be removed and replaced.

A SME needle that has been curved in the surgical site could be pulled back through the cannula (as shown in FIG. 5) even if h were two or three times the inside diameter of the cannula, since the needle flexes toward a straightened geometry in response to the constraint imposed by the rigid cannula walls.

An important characteristic of the SMAs used for the needles of this invention is that they have sufficient strength. More particularly, they should have the strength in their high temperature phase. (If the strength of the alloy is only slightly less than that of conventional needle material (e.g. stainless steel), a slightly larger needle diameter may be used to compensate, but substantially larger diameters are undesirable.) The constraint that this imposes on the phase transformation characteristics of the needle can be understood with reference to FIG. 1.

At the surgical site, the needle is heated from a temperature at or below $A_s$ to a temperature above $A_f$. When the heat is removed, the temperature should not fall below about $M_s$, lest the needle become weaker. Thus, the alloy used for SME surgical needles preferably undergoes its phase transformation in a narrow range near normal body temperature. Since practical and medical reasons limit the temperature to which the needle can be heated at the surgical site, the alloy is preferably austenitic above about 35°. ($A_f$ 35° C.). If the needle temperature rises above $A_s$ during storage, shipment, or insertion through the cannula, it would undesirably tend to curve prematurely. Although this tendency can be counteracted by refrigeration and/or maintaining the needle in a rigid sheath having a narrow lumen, for handling convenience $A_s$ is preferably about 25° C. or more.

A variety of SMAs have been identified that are suitable to a greater or lesser degree for SME surgical needles. Preferred alloys comprise nickel and at least one of aluminum, cobalt and titanium, in which the low temperature state is martensitic and the high temperature state is austenitic. Among these are Nitinol alloys, which are primarily nickel and titanium (generally about 50% each), but may also include small amounts of iron; alloys of nickel, titanium nd cobalt; and alloys of about 63% nickel and about 37% aluminum. Also suitable are stainless steel alloys that are iron-based and include one or more of chromium, nickel, manganese, silicon, and cobalt. Particularly preferred alloy compositions include 9% chromium, 10% max. nickel, 15% max. manganese, 7% max. silicon, and balance iron.

The SME surgical needles of the present invention can be fabricated in all the forms known in the surgical needle art. For example, at its distal end, the needle may have a tapered point, a triangulated point, or a combination of the two. The needle may have a flattened area over part of its length, to facilitate gripping or orienting the needle, and it may have a hole or channel at is proximal end to facilitate suture attachment.

EXAMPLE 1

In vitro

A Nitinol alloy wire of composition 50% (atomic) nickel, 50% titanium and about 1 mm in diameter, was wrapped around a 15 mm diameter threaded rod, tempered at 425° C. for about 5 min., and then cooled to −75° C. 35 mm pieces were cut, straightened, and pointed. The needles were placed in a pelvitrainer to simulate an endoscopic surgical site and then curved by heating with a laser or a cautery.

EXAMPLE 2

In vivo

A straightened needle prepared as in Example 1 was passed through an Endopath* 7 mm cannula to an operative site in a pig. It was heated by an illumination light and thereby bent into a half circle loop of diameter about 23 mm. The needle was removed from the operative site by pulling it through the cannula with a needle holder.

We claim:

1. A method for introducing a curved needle to a surgical site in a patient, comprising the steps of
   (a) inserting a cannula into the patient to permit access from outside the patient to the surgical site,
   (b) providing a shape-metal-alloy needle that, having been formed into an arc shape and tempered at an elevated temperature, has been formed into an elongated shape while in a first, low-temperature state,
   (c) passing the elongated needle through the cannula, and
   (d) heating the needle to a temperature at which the alloy is converted to a second, high temperature state, thereby causing the needle to return to the arc shape.

2. The method of claim 1 in which the needle is heated to the high-temperature state with an illumination light.

3. The method of claim 1 in which the needle is heated to the high-temperature state with a laser.

4. The method of claim 1 in which the needle is heated to the high-temperature state with a cautery.

5. The method of claim 1 further comprising removing the needle through the cannula.

* * * * *